United States Patent
Langlois et al.

(10) Patent No.: US 9,638,673 B2
(45) Date of Patent: May 2, 2017

(54) ULTRASONIC TESTING INSTRUMENT WITH DITHERY PULSING

(71) Applicant: Olympus NDT, Inc., Waltham, MA (US)

(72) Inventors: Pierre Langlois, Quebec (CA); Benoit Cournoyer, Quebec (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 750 days.

(21) Appl. No.: 13/654,969

(22) Filed: Oct. 18, 2012

(65) Prior Publication Data

US 2014/0109675 A1    Apr. 24, 2014

(51) Int. Cl.
*G01N 29/22* (2006.01)
*G01N 29/34* (2006.01)
*G01N 29/44* (2006.01)

(52) U.S. Cl.
CPC ......... *G01N 29/343* (2013.01); *G01N 29/449* (2013.01); *G01N 29/4463* (2013.01)

(58) Field of Classification Search
CPC ............. G01N 29/343; G01N 29/4463; G01N 29/449; G01N 29/341
USPC ................................................ 73/596; 702/48
See application file for complete search history.

(56) References Cited

U.S. PATENT DOCUMENTS

| | | | | |
|---|---|---|---|---|
| 3,557,354 A * | 1/1971 | Trimble | ........................ | 702/194 |
| 5,059,959 A * | 10/1991 | Barry | ............................ | 345/168 |
| 6,204,663 B1 * | 3/2001 | Prammer | ...................... | 324/303 |
| 6,462,705 B1 * | 10/2002 | McEwan | ............. | G01S 13/0209 |
| | | | | 342/118 |
| 7,254,494 B2 * | 8/2007 | Botter | ............................ | 702/48 |
| 2011/0132092 A1 * | 6/2011 | Thomas | ........................ | 73/627 |

* cited by examiner

*Primary Examiner* — Paul West
*Assistant Examiner* — Xin Zhong

(57) ABSTRACT

Disclosed is an ultrasonic device optimized with both averaging and dithery pulsing techniques. The averaging technique significantly removes white noise; on the other hand, the dithery pulsing significantly removes acoustic noise, which is otherwise accumulated during conventional averaging processes.

14 Claims, 5 Drawing Sheets

ULTRASONIC TESTING INSTRUMENT WITH DITHERY PULSING

FIELD OF THE INVENTION

The present invention relates to non-destructive testing and inspection devices (NDT/NDI) and more particularly to an ultrasonic device with noise reduction by employing techniques of dithery pulsing and averaging.

BACKGROUND OF THE INVENTION

In ultrasonic testing, a single element (conventional UT) or multiple elements such as phased array instruments are used to pulse on an object. The resulting echoes are received by the elements, digitized and analyzed to highlight any flaws in the targeted test object. Each element can be used to both send and receive high-frequency sound waves or echo signals, or they can be paired so that one element acts as a transmitter, the other one as a receiver.

Noises in echo signals are of normal presence in most types of ultrasonic testing. They are mixed in the echo signals but are not representative of the characteristics of the test objects. White noise can be from many sources such as thermally originated noise due to heat from electronics components. Existing efforts have been made to remove white noise.

In one existing effort, to help remove white noise, one could make many acquisitions then average out the response signals instead of pulsing only once. However, after every acquisition, the subsequent waveform inherits the previous waveforms' left-over energy, which is call "acoustic noise" in the processing channel. Therefore the challenge remains to remove or eliminate to the greatest degree both white noise and acoustic noise.

Averaging is made in another existing effort by means of digital processing for reducing white noise. All pulses are sent at a predetermine time step (Time "T") with equal time intervals. Averaging is done for the multiple pulses fired. The resulting signals in the previous acquisition windows capturing each previous pulse are added to the subsequent acquisition windows. Unfortunately, for example, when the second pulse starts, there is still remaining acoustic energy called acoustic noise (or "tail") left from the first pulse. The resulting signal inside the second acquisition window will then be corrupted by the "tail" of the first acquisition window. One skilled in the art can appreciated that the closer (in time) the pulses are to each other, the more acoustic noise will remain for the next pulse. This effect of acoustic noise resulted from conventional averaging will be further illustrated in the detailed description, in comparison to that to be minimized by using the solution herein disclosed.

U.S. Pat. No. 3,557,354 uses averaging to improve signal to noise ratio and reduce white noise. But it does not involve any effort in reducing acoustic noise caused by the accumulation process.

Another existing effort also found in U.S. Pat. No. 7,254,494 (later as '494) in which time shifting sequence of bursts (of ultrasound) is used to improve signal to noise ratio. However, '494 does not use averaging in its processing, instead deploys a method to identify the pattern of the sequence of burst, and then uses the information on the pattern for noise reduction.

It would be therefore adventurous to reduce white noise in ultrasonic testing devices by using averaging in digital data process, and address the drawbacks of previous effort by eliminating acoustic noise accumulated during the conventional averaging process.

SUMMARY OF THE INVENTION

It is therefore an objective of the present disclosure to improve the accuracy of ultrasonic testing instrument by significantly reducing acoustic residual noise (later as acoustic noise) accumulated during averaging processes used in some ultrasonic testing instruments.

It is another objective of the present disclosure to reduce the acoustic noise by causing the acoustic noise from all previous pulses become uncorrelated, so that the acoustic noise from each pulsing has the effect of cancelling each other, instead of being augmented during the averaging or summation process having many acquisition events.

It is yet another objective of the present disclosure to employ dithery pulsing technique to de-correlate acoustic noise from each acquisition event so that acoustic noises can be decimated during a number of acquisition events.

The inspection device according to the present invention is coupled with a probe configured to pulse detective energy, such as ultrasound to a test object during a testing cycle with N pulses to produce and receive N set of wave responses, and to produce therefrom N sets of electric echo signals. A least one analog to digital converter is configured to digitize the N sets of echo signals and to produce therefrom N sets of digitized signal samples, which correspond respectively to N sets of acquired signal samples and N sets of noise signal samples representing the acoustic noise. A digital logic device or processor having a data processing unit is configured to execute an averaging process by which the N sets of signal samples are summed and averaged to produce a final testing result. Further the digital logic device comprises a pulser controller configured to control the pulsing according to a dithery pulsing sequence by which the probe is pulsed in a dithery pattern between one pulse and another so that the combination effect of the N sets of the noise signal samples is decimated during the averaging process and in the testing result.

DESCRIPTION OF THE INVENTION

Figure 1:
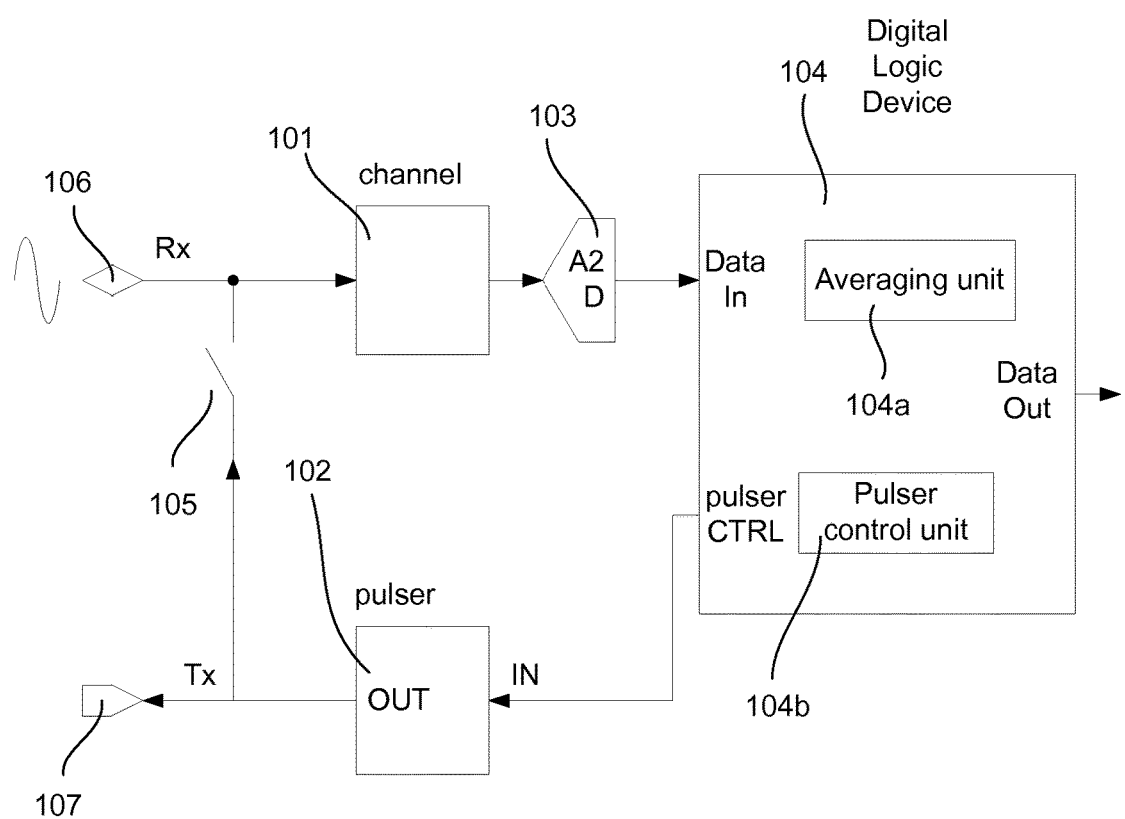
FIG. 1 is a schematic diagram of the preferred embodiment used for an ultrasonic Instrument, employing dithery pulsing and averaging in data processing.

Referring to FIG. 1, the preferred embodiment according to the present disclosure used for an ultrasonic instrument is shown to preferably comprise a transducer 106, an analog channel 101, a pulser 102, an analog to digital (A2D) converter 103 and a digital logic device 104. Logic device 104 further comprises an averaging component 104a and a pulser control unit 104b controlling pulser 102.

If a single element is used to transmit and receive, it will be plugged in a transceiver or a receiver 106 with a switch 105 closed. If two elements are paired, the receiver will be connected to 106 and a transmitter 107. The usage of probe element shown in FIG. 1 is for an exemplary case only. Many other combinations of transmitter, receiver or transceiver and design of single, dual or array elements can be used and the scope of the present disclosure is not restricted in this regard. To start the acquisition, digital logic device 104 uses pulser 102 through pulser control unit 104b to send the first high-frequency pulse to transmitter 107 (and 106 if switch 105 is closed). The echoes come back into analog channel 101 to be processed with gain and filtering processes, then further fed into analog to digital converter 103. The Digital Logic Device 104 stores the data for future use, such as averaging by an averaging unit 104a. This whole process is executed for N times for one testing cycle during N acquisition events where N is the averaging factor. After N times of this process, the averaged result is packaged and sent to a display unit (not shown) to display to the operator.

Figure 2:
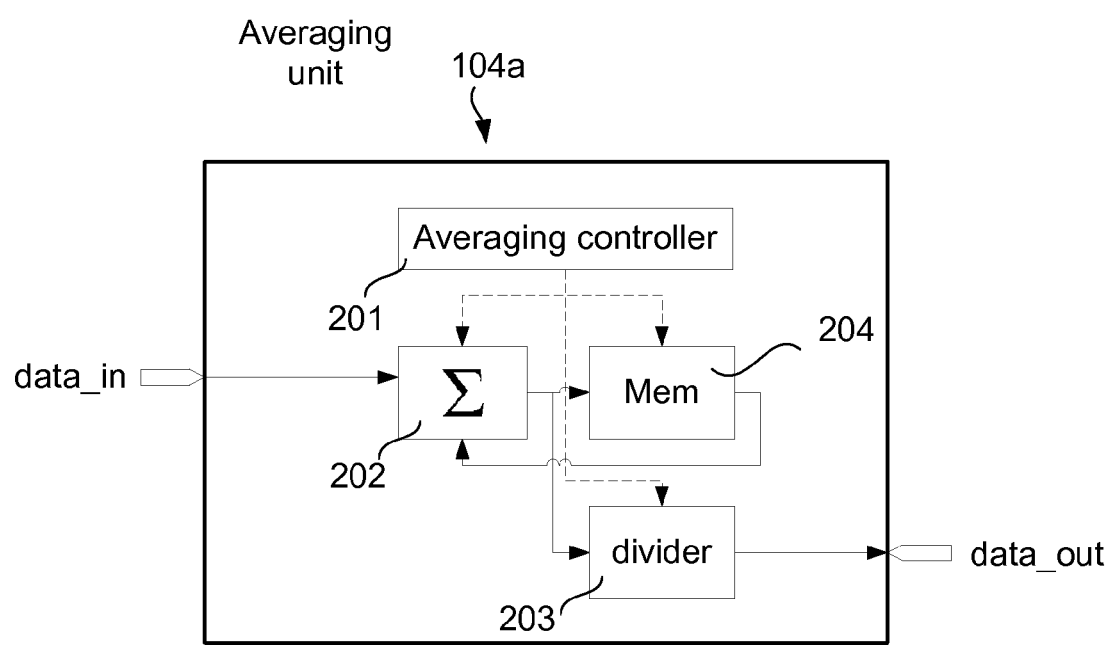
FIG. 2 is a schematic diagram depicting a circuit component performing the averaging function according to the present invention.
Figure 4:
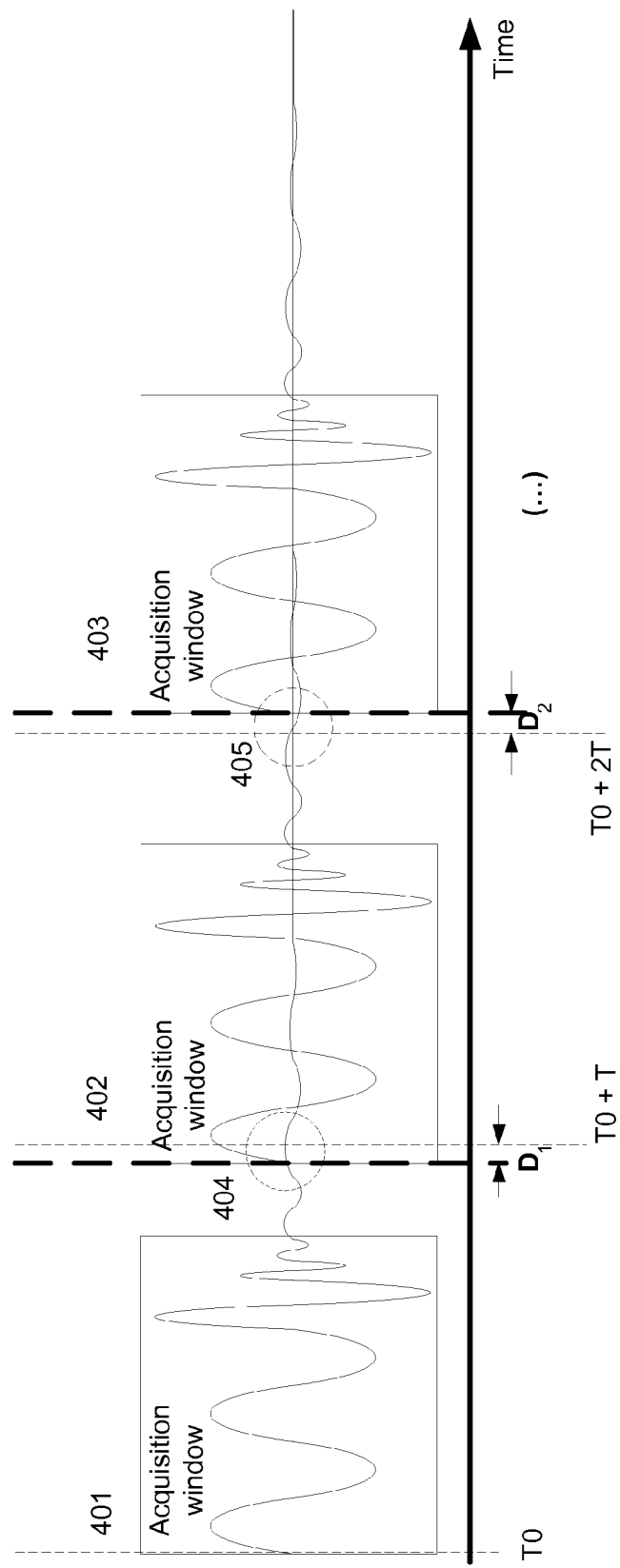
FIG. 4 is a diagram illustrating waveforms of an averaging process with dithery pulsing during an acquisition cycle according to the present invention.

Referring to FIG. 2, averaging unit 104a according to present disclosure is elaborated. The averaging unit can be designed to work in ways known to those skilled in the art. The following exemplary case is given for illustration purpose and the averaging function is not limited in this regard. In an exemplary case, digitized data from the first pulse is stored directly in a memory 204. On a second pulse, the data from the first pulse is selected in the memory 204 and added by an adder 202 to the current data. The new value is stored in memory 204. An averaging controller 201 selects the right address of the memory for all the pulses. Once the data is collected for N times as specified by the operator, the averaging is done and averaging controller 201 selects the right divider 203 that corresponds to N (chosen by the operator). N is preferably a number of a power of two. FIG. 4 later in the present disclosure shows the effect of this averaging in waveform diagrams, giving illustration of the averaging process.

Figure 3:
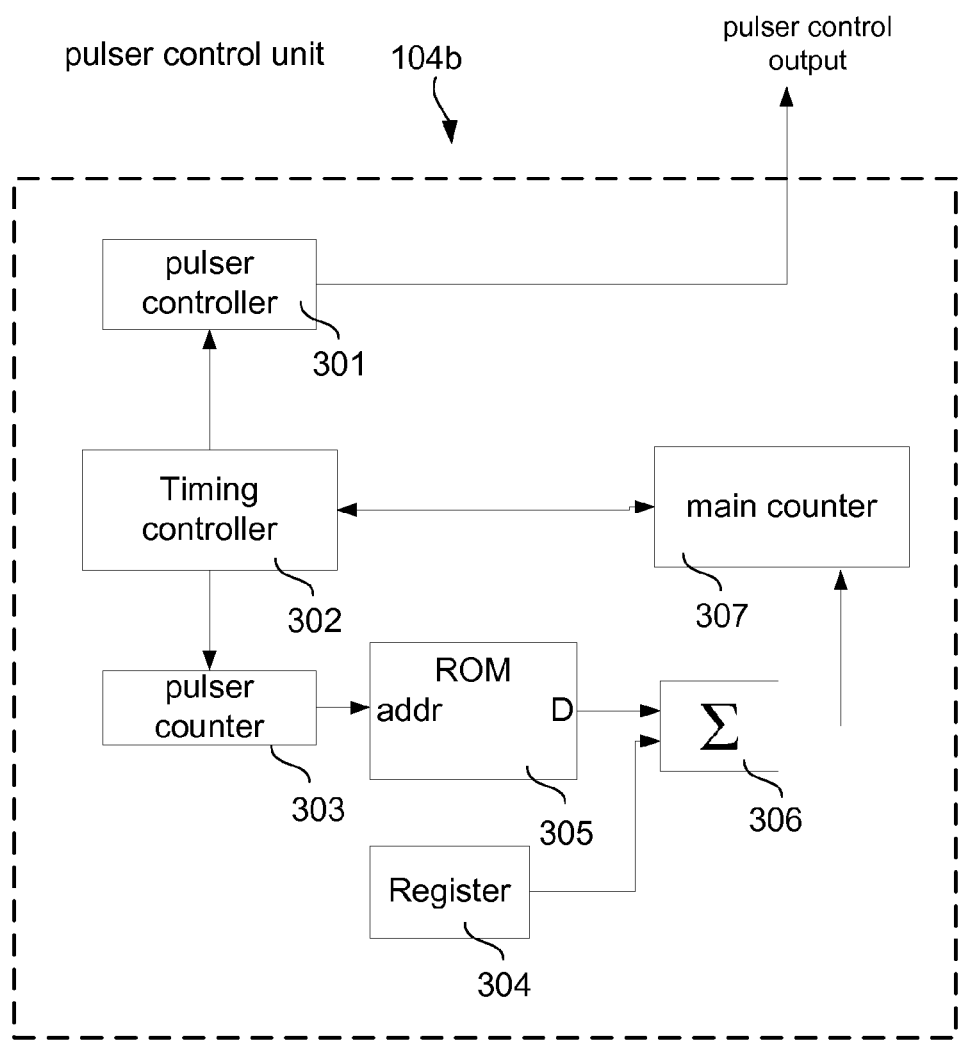
FIG. 3 is a schematic diagram depicting a circuit component performing the dithery pulsing function according to the present invention.

Reference is now made jointly to FIG. 3 and FIG. 4. FIG. 3 shows how pulser control unit 104b works. FIG. 4 shows the waveforms of a series of acquisition events led by a series of pulsing for a testing cycle. Dithering pulsing is carried out with pulses sent at each time interval T dithered with $D_n$.

As shown in FIG. 3, a timing controller 302 starts the first acquisition using a pulser controller 301 to drive the pulser 102 outside the digital logic device. A register 304 contains the pulse time interval T. ROM 305 contains dither value $D_n$, for the respective acquisition event. Then a main counter 307 starts counting until it reaches the $T+D_n$ for each acquisition event shown in FIG. 4 before it re-starts again for a new subsequent acquisition event led by a subsequent pulsing. When $T+D_n$ is achieved by adder 306 which adds the value from register 304 and $D_n$ value from ROM 305. The address of the ROM is controlled by a pulse counter 303 which is incremented at every pulse.

It is conceivable that it is the same effect whether the main counter 307 starts to count from $T_0$ and continue to add nT for each acquisition event, or to restart counting for each acquisition event as above described. For the case of continuous counting, the pulsing points or the dithery pulsing sequence is governed by $T_0+nT+D_n$, wherein n=1~N, with n to be sequence number at which the probe is pulsed and N to be averaging factor and $D_n$, is the dither value which much less than T. $T_0$ is the initial starting point of the whole test. It should be appreciated that the dithery pulsing sequence can be implemented by counter 307 and timing control mechanism herein presented in different ways which all remain within the framework of present invention.

In one averaging process shown in FIG. 2, values $D_n$, preferably dither randomly off zero from pulse to pulse or, at least dither with pairs of positive and negative equal values. There are many ways to make the dithery sequence and assign $D_n$, values. The following two tables give examples of value $D_n$, for an averaging factor of N=8. As shown in Table-1, dither values can be random numbers. However, with limited averaging factor, it should noted that care should be given so that the sum of all positive dither values should be roughly equal to the sum of negative dither values in one averaging process. In another example as shown in Table-2, dither values can be pairs of negative and positive equal values.

TABLE 1

Random dither value $D_n$ for each pulse

| Pulser Number n | $D_n$ |
|---|---|
| 1 | −310 ns |
| 2 | +280 ns |
| 3 | −160 ns |
| 4 | +180 ns |
| 5 | +80 ns |
| 6 | −90 ns |
| 7 | +40 ns |
| 8 | −40 ns |

TABLE 2

Dither values in pairs of positive and negative equal values

| Pulser number | D |
|---|---|
| 1 | −300 ns |
| 2 | +300 ns |
| 3 | −100 ns |
| 4 | +100 ns |
| 5 | −300 ns |
| 6 | +300 ns |
| 7 | +100 ns |
| 8 | −100 ns |

Referring now more specifically to FIG. 4, three acquisition events, with three acquisition windows showing waveform of echo signals of from three pulses are illustrated. Acquisition windows are the time frames in which digitized data sample are selected to use in the averaging process. One testing can include N acquisition events, wherein N is the averaging factor as aforementioned. It should be noted that in this context, the same numeral used for respective pulses, waveforms and acquisition windows. For example, pulse 401 and waveform 401 denote to the respective pulse and waveform in the same acquisition event.

During the averaging process, waveform 401 in the respective acquisition window (401) is added to waveform 402 in acquisition window 402, and so forth for all the pulses. Unfortunately, when pulse 402 starts, as one can note that there is still acoustic noise (or "tail") from the last pulse 401. The desired signal inside the acquisition window will then be corrupted by the "tail" of 401. This effect is made more obvious in enlarged illustrations 404 and 405 shown in FIG. 5.

Figure 5:
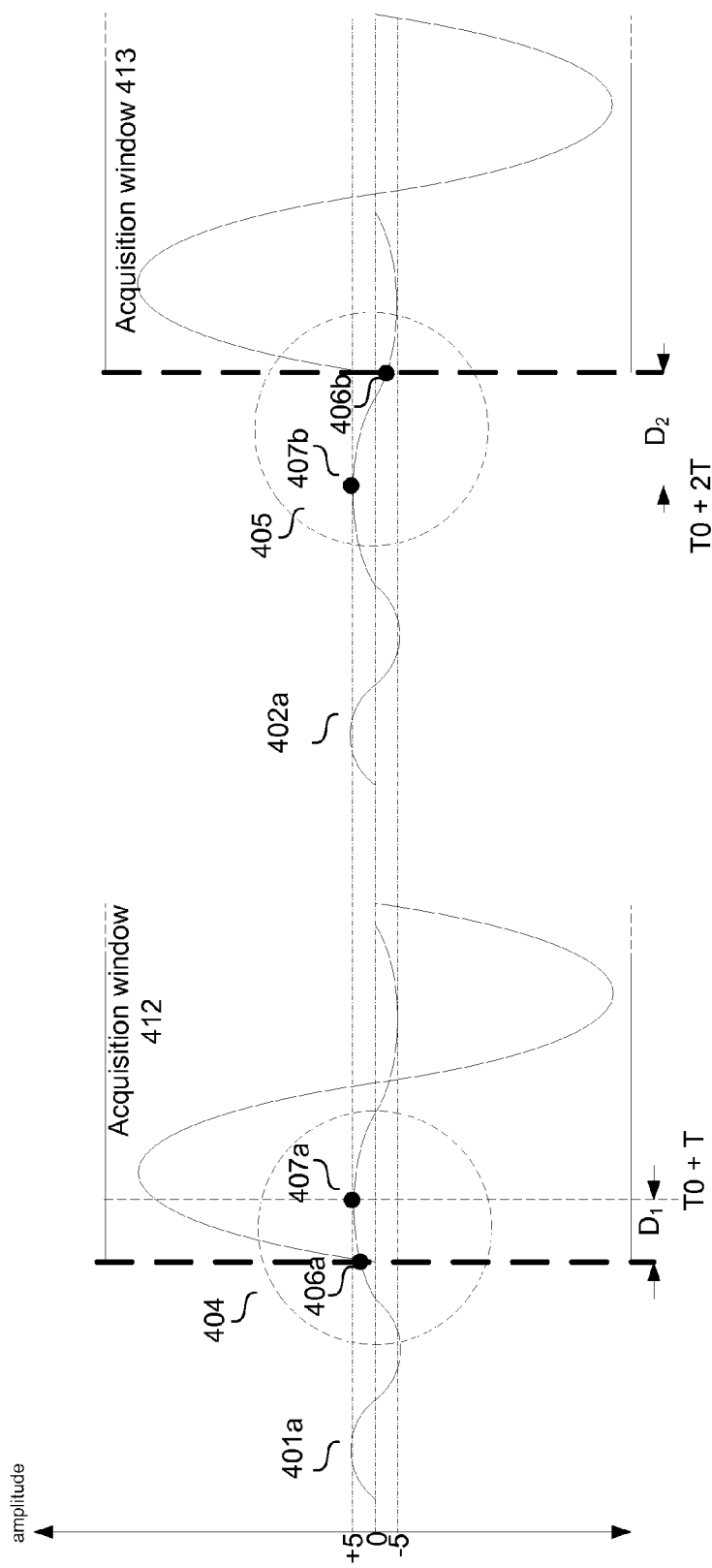
FIG. 5 is a diagram with an enlarged illustration showing the effect how the acoustic noise is reduced during the averaging process in FIG. 4. contributed to dithery pulsing.

Further referring to FIG. 5 which shows that if the pulses are triggered always at a fixed time interval, which is a multiple of time T, the same part of the tails from the last pulse are added to the echo of the current pulse in the acquisition window. For example, the intersection of the tail 401a and T0+T, 407a is the same as intersection of 402a and T0+2T, 407b. Summing all the acquisition windows at fixed timer intervals will include the echo (desired signal) and unwanted acoustic noise (the remaining "tails"). The closer (in time) the pulses are to each other, the more acoustic noise will remain for the next pulse, due to larger residual amplitude left in the "tails". This is why existing or conventional averaging process adds acoustic noise into the test results.

The dithery pulsing executed by the preferred embodiment shown in FIG. 3 adds an important novel aspect to conventional averaging and reduces or significantly eliminates acoustic noise in test results. As can be seen in FIG. 4, particularly in an enlarged illustration in FIG. 5, the effect of dithery pulsing by shifting or dithering the time at which the pulses are fired effectively cancels the acoustic noise. Dithering of pulse timing removes the correlation between the pulses and the acoustic noise. This scheme transforms the acoustic noise into white noise. Instead of pulsing at fixed time interval, or at multiple of T, one could pulse at time $T+/-D_n$ where $D_n$, varies at every pulse.

An example is shown in FIG. 4. The first three pulses are shown (401, 402 and 403). The number of pulses is determined by the averaging factor N. This factor is usually determined by the operator who takes several factors into consideration, such as the desired precision and the frequency of the acquisitions (PRF). The acoustic noise from the previous pulse is sampled at different times ($T-D_1$ and $T+D_2$). When averaging all the pulses, the remaining acoustic noise will tend to be eliminated, because it is sampled at different moment.

Referring to FIG. 5, an exemplary case of the "tails" is illustrated with an enlarged scale. Preferably, the waveforms at each acquisition windows all start to amplitude zero, without the influence of residual acoustic energy from the last pulse. If the pulses would have occurred at a fixed time interval, at every time T, the amplitude of the acoustic noise for the first sampled would be equal in each acquisition window. In FIG. 5, it would be amplitude of +5 for point 407a and 407b. This means that for the first three pulses, the acoustic noise error added is (0+5+5)/3=3.33. With the dithery scheme employed by the present disclosure, the amplitude of the acoustic noise varies at randomly dithered intervals. In this case, 406a is of amplitude 3 at $T_0+T-D_1$ and 406b is of amplitude −2 at $T_0+T+D_2$. The more acquisition windows there are and the more cycles of averaging there will be, the closer to white noise the acoustic noise will be. As an exemplary case of the first three pulses shown here, the acoustic noise error is (0+3−2)/3=0.33, which is 10 times smaller than that of without dithering as disclosed in the present invention.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A non-destructive inspection or testing (NDT/NDI) device configured for inspecting a test object, comprising:
a probe configured for pulsing a test object during a testing cycle at a testing location with N pulses to produce and receive N sets of wave responses, and to produce therefrom N sets of electric echo signals;
at least one analog to digital converter configured to digitize the N sets of echo signals and to produce therefrom N sets of digitized signal samples, which correspond respectively to N sets of acquired signal samples and N sets of noise signal samples;
a digital logic device, having a data processing unit configured to execute an averaging process by which the N sets of signal samples are summed and averaged to produce a final testing result;
wherein each one of the N sets of noise signal samples includes a residual acoustic energy from a previous one of the N sets of noise signal samples,
wherein the digital logic device further comprises a pulser control unit configured to control the pulsing according to a dithery pulsing sequence by which the probe is pulsed in a random dithery manner given by a plurality of dither values which are independent between one pulse and another so that the combination effect of the residual acoustic energy from the N sets of the noise signal samples is decimated during the averaging process and in the testing result,
wherein the averaging process is conducted regardless of the dithery pattern, and,
wherein the dithery pulsing sequence is governed by $T_0+nT+D_n$, wherein n=1~N, with n to be a sequence number at which the probe is pulsed, $T_0$ to be a starting time of the pulsing, T to be a pulse time interval between two adjacent pulses, and $D_n$ are the dither values.

2. The device of claim 1, wherein N is an averaging factor used by the digital logic device for the averaging process.

3. The device of claim 1, wherein the digital logic device further comprises an averaging unit for executing the averaging process, the averaging unit further including an averaging controller, a digital memory, an adder and a divider.

4. The device of claim 1, wherein the pulser control unit further comprises a timing controller, a pulser counter, a timing adder, a main counter and pulser controller to apply the dithery pulsing.

5. The device of claim 1, wherein the probe includes a single element ultrasonic transmitter.

6. The device of claim 1, wherein the probe includes a single element transceiver.

7. The device of claim 1, wherein the probe is a dual element probe.

8. The device of claim 1, wherein the probe is a phased array probe.

9. A method of pulsing a non-destructive inspection or testing (NDT/NDI) device having a probe configured for pulsing a test object during a testing cycle, the method comprises the steps of:
pulsing the probe with N pulses according to a pulsing sequence,
causing the probe to receive N sets of wave responses, and to produce therefrom N sets of electric echo signals;
digitizing the N sets of echo signals to produce N sets of digitized signal samples, which correspond respectively to N sets of acquired signal samples and N sets of noise signal samples, wherein each one of the N sets of noise signal samples includes a residual acoustic energy from a previous one of the N sets of noise signal samples;
averaging said N sets of acquired signal samples using a digital logic component;

wherein the pulsing sequence has a random dithery manner given by a plurality of dither values which are independent between one pulse and another so that the combination effect of the residual acoustic energy from the N sets of the noise signal samples is decimated during the averaging step and in the testing result, wherein the averaging process is conducted regardless of the dithery pattern, and, wherein the dithery pulsing sequence is governed by $T_0+nT+D_n$, wherein $n=1\sim N$, with n to be a sequence number at which the probe is pulsed, $T_0$ to be a starting time of the pulsing, T to be a pulse time interval between two adjacent pulses, and $D_n$ are the dither values.

10. The method of claim 9, wherein the steps of pulsing, digitizing and averaging are executed by a digital logic device.

11. The method of claim 10, wherein the digital logic device further comprises an averaging unit for executing the averaging process, the averaging unit further including an averaging controller, a digital memory, an adder and a divider.

12. The method claim 10, wherein the logic device further comprising a pulser control unit which further comprises a timing controller, a pulser counter, a timing adder, a main counter and pulser controller to apply the dithery pulsing.

13. The method claim 1, wherein the probe includes a single element ultrasonic probe.

14. The method claim 1, wherein the probe is a multiple or array element ultrasonic probe.

* * * * *